(12) United States Patent
Gajji et al.

(10) Patent No.: US 10,444,134 B2
(45) Date of Patent: Oct. 15, 2019

(54) VISCOSITY MEASUREMENT

(71) Applicant: Halliburton Energy Services, Inc., Houston, TX (US)

(72) Inventors: Bhargav Gajji, Cypress, TX (US); Ketan Chimanlal Bhaidasna, Houston, TX (US); Richard Gary Morgan, Channelview, TX (US); Subrahmanyam Surya Venkata Sista, Hyderabad (IN); Chatti Srinivasa Rao, Hyderabad (IN)

(73) Assignee: Halliburton Energy Services, Inc., Houston, TX (US)

(*) Notice: Subject to any disclaimer, the term of this patent is extended or adjusted under 35 U.S.C. 154(b) by 190 days.

(21) Appl. No.: 15/543,111

(22) PCT Filed: Mar. 26, 2015

(86) PCT No.: PCT/US2015/022707
§ 371 (c)(1),
(2) Date: Jul. 12, 2017

(87) PCT Pub. No.: WO2016/153517
PCT Pub. Date: Sep. 29, 2016

(65) Prior Publication Data
US 2018/0010995 A1    Jan. 11, 2018

(51) Int. Cl.
*G01N 11/14* (2006.01)

(52) U.S. Cl.
CPC ........ *G01N 11/14* (2013.01); *G01N 2011/147* (2013.01)

(58) Field of Classification Search
CPC ... G01N 11/14; G01N 2011/147; G01N 11/00
See application file for complete search history.

(56) References Cited

U.S. PATENT DOCUMENTS

| | | | |
|---|---|---|---|
| 6,629,451 B1 * | 10/2003 | Taylor | G01N 11/14 73/54.28 |
| 7,287,416 B1 | 10/2007 | Bi | |
| 8,813,542 B1 | 8/2014 | Bi | |
| 8,850,874 B1 | 10/2014 | Bi | |
| 2009/0216465 A1 | 8/2009 | Millet | |
| 2010/0071442 A1 | 3/2010 | Moon, Jr. et al. | |

OTHER PUBLICATIONS

International Preliminary Report on Patentability issued in related PCT Application No. PCT/US2015/022707, dated Oct. 5, 2017, 11 pages.
International Search Report and Written Opinion issued in related PCT Application No. PCT/US2015/022707 dated Dec. 9, 2015, 14 pages.

* cited by examiner

*Primary Examiner* — David Z Huang
(74) *Attorney, Agent, or Firm* — Tenley Krueger; Baker Botts L.L.P.

(57) ABSTRACT

A system for measuring the viscosity of a fluid comprises a rotor cup; a bob disposed within the rotor cup and having shaft rotatably coupled to the rotor cup; a bearing connecting the shaft of the bob to the rotor cup; a magnetic coupling comprising a first magnetic element connected to the shaft of the bob and a second magnetic element disposed outside the rotor cup adjacent to the first magnetic element; and an inertial measurement unit disposed adjacent to the second magnetic element which is capable of sensing rotation of the magnetic coupling.

20 Claims, 2 Drawing Sheets

VISCOSITY MEASUREMENT

CROSS-REFERENCE TO RELATED APPLICATION

The present application is a U.S. National Stage Application of International Application No. PCT/US2015/022707 filed Mar. 26, 2015, which is incorporated herein by reference in its entirety for all purposes.

BACKGROUND

The present disclosure relates generally to well drilling operations and, more particularly, to evaluate the properties of the fluids used in well drilling operations.

Hydrocarbons, such as oil and gas, are commonly obtained from subterranean formations that may be located onshore or offshore. The development of subterranean operations and the processes involved in removing hydrocarbons from a subterranean formation are complex. Typically, subterranean operations involve a number of different steps such as, for example, drilling a wellbore at a desired well site, cementing the well, treating the wellbore to optimize production of hydrocarbons, and performing the necessary steps to produce and process the hydrocarbons from the subterranean formation.

Various types of fluids are used in the oil and gas industry. Non-limiting examples include drilling muds, cement slurries, and stimulation treating fluids. Such fluids are typically pumped into oil or gas wells in known manners. It is desirable to know various characteristics of the fluids to determine how such fluids will act upon being pumped and placed in, or circulated through, the wells. For example, fluids used downhole are often exposed to unique conditions, including high pressures and temperatures.

Viscosity, elasticity, and consistency are rheological characteristics that sometimes need to be measured for a given fluid. Known devices used to test fluids for these characteristics include viscometers, rheometers, and consistometers. However, downhole pressures and temperatures may change the characteristics of a fluid. As a result, the fluid characteristics measured at the surface may be inconsistent with how the fluid behaves within the well environment. Fluids are typically chosen for an operation based on favorable properties, such as an ability to suspend particulates. It is therefore desirable to measure fluid properties, including viscosity, of a downhole fluid under downhole conditions before the fluid is placed in the well.

FIGURES

Some specific exemplary embodiments of the disclosure may be understood by referring, in part, to the following description and the accompanying drawings.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such as wires, optical fibers, microwaves, radio waves, and other electromagnetic and/or optical carriers; and/or any combination of the foregoing.

Illustrative embodiments of the present disclosure are described in detail herein. In the interest of clarity, not all features of an actual implementation may be described in this specification. It will of course be appreciated that in the development of any such actual embodiment, numerous implementation-specific decisions are made to achieve the specific implementation goals, which will vary from one implementation to another. Moreover, it will be appreciated that such a development effort might be complex and time-consuming, but would, nevertheless, be a routine undertaking for those of ordinary skill in the art having the benefit of the present disclosure.

The terms "couple" or "couples" as used herein are intended to mean either an indirect or a direct connection. Thus, if a first device couples to a second device, that connection may be through a direct connection or through an indirect mechanical or electrical connection via other devices and connections. Similarly, the term "communicatively coupled" as used herein is intended to mean either a direct or an indirect communication connection. Such connection may be a wired or wireless connection such as, for example, Ethernet or LAN. Such wired and wireless connections are well known to those of ordinary skill in the art and will therefore not be discussed in detail herein. Thus, if a first device communicatively couples to a second device, that connection may be through a direct connection, or through an indirect communication connection via other devices and connections.

Figure 1:
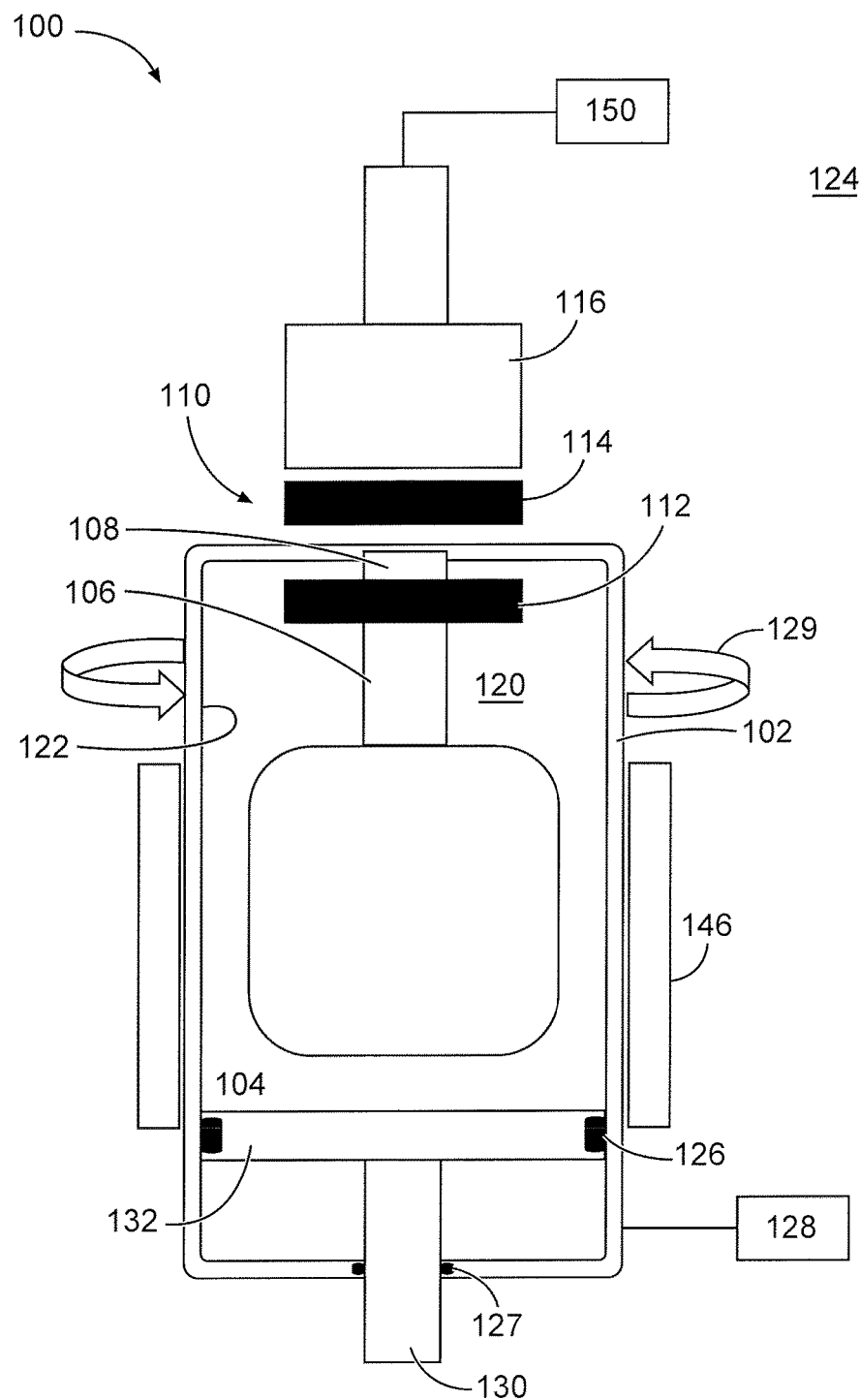
FIG. 1 is a diagram showing an illustrative viscosity measurement system, according to aspects of the present disclosure.

FIG. 1 shows a viscosity measurement system 100. The system 100 may comprise a rotor cup 102, a bob 104 disposed within the rotor cup 102, and a shaft 106 rotatably coupled to the rotor cup 102. A bearing 108 may connect the shaft 106 to the rotor cup 102. The bearing 108 may be structured and arranged to allow the shaft 106 and the bob 104 to rotate inside the rotor cup 102 substantially independent of the rotor cup 102. In certain embodiments, the bearing 108 may comprise a jewel bearing.

The system 100 may comprise a magnetic coupling 110. The magnetic coupling 110 may comprise a first magnetic element 112 connected to the shaft 106 and a second magnetic element 114 disposed outside the rotor cup 102 and adjacent to the first magnetic element 112. An inertial measurement unit (IMU) 116 may be disposed adjacent to the second magnetic element 114. The IMU may measure acceleration, velocity, and/or position of the second magnetic element 114.

Rotation of the first magnetic element 112 may cause rotation of the second magnetic element 114. As such, rotation of the first magnetic element 112 may cause the magnetic coupling 110 to rotate. The IMU 116 may be capable of sensing rotation of the magnetic coupling 110. For example, the IMU 116 may be capable of rotation properties of the magnetic coupling (such as angular velocity and angular acceleration), which may be indicative of corresponding rotation properties of the bob 104.

In certain embodiments, the rotor cup 102 may comprise an inner chamber 120 enclosed within the rotor cup 102 and defined by an inner surface 122 of the rotor cup. A fluid may be contained within the inner chamber 120. For example, in certain embodiments, the inner chamber 120 may be completely enclosed by the rotor cup 102 and substantially separated from a surrounding environment 124.

In certain embodiments, the system 100 may comprise a piston seal 126 located between the piston 132 and the rotor cup inner surface 122. In certain embodiments, the system 100 may comprise a piston rod seal 127 between the piston rod 130 and the rotor cup 102.

In certain embodiments, a heater 146 may be disposed adjacent to the rotor cup 102. The heater 146 may be capable of raising the temperature of the rotor cup 102 and/or fluid within the inner chamber 120. For example, the heater 146 may be capable of bringing the temperature of the rotor cup 102 and/or fluid within the inner chamber 120 within the range of 25° C. to 250° C.

In certain embodiments, a motor 128 may be connected to the rotor cup 102. The motor 128 may be capable of rotating the rotor cup 102 about the bob 104. For example, the motor 128 may axially rotate 129 the rotor cup 102 by applying a torque to the rotor cup 102. The motor 128 may be capable of rotating the rotor cup 102 at a constant angular velocity. For example, the motor 128 may rotate the rotor cup 102 at a set point velocity determined by an operator. In certain embodiments, the motor 128 may linearly accelerate the rotation of the rotor cup 102 until the angular velocity of the rotor cup 102 reaches the set point velocity, and then maintain the angular velocity of the rotor cup 102 at the set point velocity. In certain embodiments, the motor 128 may be capable of non-linearly accelerating the rotor cup 102 angular velocity (e.g., exponentially increasing the angular velocity of the rotor cup 102).

In certain embodiments, a piston rod 130 may extend into the rotor cup 102. The piston rod 130 may be attached to a piston 132 disposed within the rotor cup 102. In certain embodiments, the inner chamber 120 may be defined within the rotor cup 102 and between the rotor cup inner wall 122 and the piston 132. For example, extending the piston rod 130 further into the rotor cup 102 may cause the piston 132 to move axially within the rotor cup 102 and reduce the volume of the inner chamber 120. In certain embodiments, the pressure within the inner chamber 120 may be increased by exerting a force on the inner chamber 120 with the piston rod 130 via the piston 132. If the fluid comprises a compressible fluid, exerting a force on the inner chamber 120 with the piston rod 130 may cause the piston 132 to axially translate within the inner chamber 120. In certain embodiments, the piston rod 130 and piston 132 may be used to increase the pressure within the inner chamber 120.

The piston rod 130 may be capable of adjusting the pressure within the inner chamber 120 through actuation of the piston rod 130. For example, the inner chamber 120 may contain a pressure above of between 0.5 atmosphere and 250 atm. For example, the inner chamber 120 may be pressurized to at least 2 atm by increasing pressure on the inner chamber with the piston rod 130 and piston 132. In certain embodiments, the inner chamber 120 may be capable of containing a pressure of at least 250 atm. In certain embodiments, the inner chamber 120 may be capable of containing a pressure of up to 500 atm.

In certain embodiments, the fluid may comprise any fluid or combination of fluids for use in a down-hole environment. For example, the fluid may comprise a mud, oil well cements, and completion gels, and other fluids for use in the down-hole environment. The fluid may comprise a Newtonian and/or non-Newtonian fluid.

In certain embodiments, a fluid may be placed in the inner chamber 120, within the rotor cup 102, where the fluid may be in contact with the bob 104. The motor 128 may axially rotate the rotor cup 102 around the bob 104. Axially rotating the rotor cup 102 may cause rotation of the fluid within the inner chamber 120 relative to the bob 104. For example, rotation of the rotor cup 102 may impart an angular shear force on the fluid, causing the fluid to rotate in the same angular direction as the rotor cup 102. The fluid moving around the bob 104 may exert a shear force on the bob 104. As such, angular rotation of the bob 104 may be dependent on the ability of the fluid to exert shear force on the bob 104 and/or the ability to impart shear force on the fluid with the rotor cup 102. This application of shear force to the fluid by the rotor cup 102 or by the fluid on the bob 104 may be dependent on the viscosity of the fluid. For example, greater viscosity of the fluid may allow greater ability to exert shear force by the fluid to the bob 104 or onto the fluid by the rotor cup 102, which would lower the delay of the bob to match the set point angular velocity of the rotor cup 102, for example when the bob is allowed to rotate from initial stationary condition. Lower viscosity may reduce the force exerted by the fluid on the bob 104 or on the fluid by the rotor cup, thereby causing a relatively slower angular acceleration of the bob 104 (where the bob would then take longer to reach a set point angular velocity of the rotor cup 102, for example when released from stationary condition).

Shear force exerted onto the bob 104 by the fluid may cause the bob 104 to rotate, which may cause the shaft 106 to rotate. Rotation of the shaft 106 may cause the magnetic coupling 110 to rotate (i.e., the shaft may rotate the first magnetic element 112, which then causes rotation of the second magnetic element 114). So, rotation properties of the magnetic coupling 110 may be indicative of the rotation properties of the bob 104.

Rotation of the magnetic coupling 110 may be measured by the IMU 116. For example, the IMU 116 may read the angular velocity of the magnetic coupling 110 and/or the angular acceleration of the magnetic coupling 110.

The IMU 116 may send measurement data containing magnetic coupling rotation measurement information to a processor 150. In certain embodiments, the IMU 116 may comprise the processor 150. In other embodiments, the processor 150 may be part of a computer separate from the IMU 116. For example, the processor 150 may be in communication with the IMU 116 and capable of receiving measurement data in real-time from the IMU 116. Also for example, the measurement data may be sent to the processor 150 on a delayed basis, e.g., the measurement data may be sent to the processor 150 after the measurement data has been completely collected by the IMU 116. The processor 150 may be configured to generate at least one operator readable output using the measurement data. For example, the processor 150 may output measurement data (e.g., instantaneous angular velocity and/or graph of angular velocity over time), and/or manipulate the measurement data to output calculated viscosity.

In certain embodiments, one or more fluids having known fluid properties, such as viscosity, may be used to calibrate the system 100. After calibration, fluids having unknown viscosity properties may be measured by the system 100. Measurements observed by the IMU 116 for fluids having unknown properties may be compared to measurements from known fluids to determine to which known fluid the unknown fluid is most similar, in terms of viscosity profile.

Figure 2:
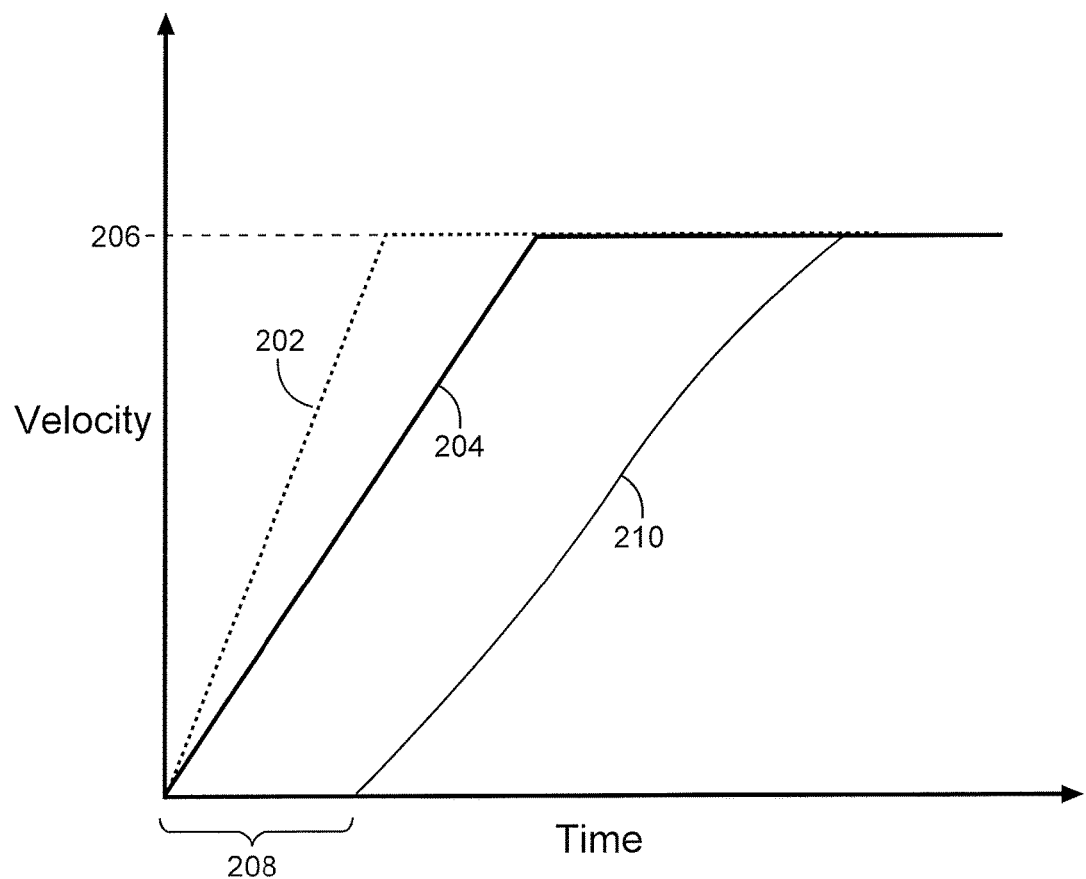
FIG. 2 is a graph illustrating a relationship of velocity of a rotor and a bob over time, according to aspects of the present disclosure.

Referring now to FIG. 2, an illustrative graph is shown with angular velocity of a rotor cup over time 202 and angular velocity of a bob over time 204. In certain embodiments, a motor may increase the angular velocity of the rotor cup containing a fluid. For example, as shown in FIG. 2, the motor may linearly increase the angular velocity of the rotor cup (i.e., apply constant angular acceleration to the rotor cup). Axial rotation of the rotor cup may rotate the fluid within the rotor cup (e.g., by imparting a shear force to the fluid). In certain embodiments, the motor may increase the angular velocity of the rotor cup up to a rotation velocity set point 206. The rotation velocity set point 206 may be determined by the operator. For example, in certain embodiments, the rotation velocity set point 206 may be from about 1 rotation per hour to about 1000 rotations per minute (rpm).

The fluid may be in contact with the bob within the rotor cup and cause the bob to rotate within the rotor cup (e.g., by exerting a shear force on the bob). The bob may rotate in response to the rotating fluid within the rotor cup. In certain embodiments, the angular velocity of the bob may increase slower than the rotor cup (i.e., the bob may have a lower acceleration than the rotor cup). The angular acceleration of the bob may depend on the viscosity/rheology of the fluid. The angular velocity of the bob may increase until it reaches the rotation velocity set point 206, where the angular velocity of the bob may be substantially the same as the angular velocity of the rotor cup.

In certain embodiments, the bob may be held in place and substantially prevented from rotating within the inner chamber by the magnetic coupling. For example, the bob may be held in place within the rotor cup during a rotor cup ramp up period 208. During the rotor cup ramp up period 208, the rotor cup may be rotated axially around the bob while the bob is substantially prevented from rotating. For example, a magnetic coupling may prevent the bob from rotating within the rotor cup during the rotor cup ramp up period 208. In certain embodiments, the rotor cup ramp up period 208 may comprise the period of time the angular velocity of the rotor cup is increased to the rotational velocity set point 206 (i.e., the time before the rotor cup reaches the rotational velocity set point 206). In certain embodiments, the rotor cup ramp up period 208 may be any amount of time delay between starting rotation of the rotor cup and releasing the bob. For example, the rotor cup ramp up period 208 may provide a set time delay (i.e., head start) between rotor cup rotation and allowing the bob to rotate within the rotor cup. During the rotor cup ramp up period 208, the fluid may begin rotating within an inner chamber of the rotor cup in response to a shear force imparted by the rotor cup.

When the bob is released and allowed to rotate, the fluid may exert a substantially higher shear force on the bob compared to that exerted when the rotor cup and bob begin rotation at the same time. After the rotor cup ramp up period 208, the angular velocity of the bob over time 210 may be measured by an IMU.

Although FIG. 2 shows linearly increasing the angular velocity of the rotor cup, non-constant acceleration may be applied to the rotor cup causing the angular velocity of the rotor cup to increase exponentially, geometrically, or other velocity profiles.

In certain embodiments, a method for measuring the viscosity of a fluid may comprise containing the fluid within a rotor cup having a bob rotatably disposed therein; rotating the rotor cup and the fluid disposed therein; sensing an angular acceleration of a magnetic coupling connected to the bob; and determining the viscosity of the fluid based on the angular acceleration of the magnetic coupling.

In certain embodiments, a method for measuring the viscosity of a fluid may comprise containing the fluid within a rotor cup having a bob rotatably disposed therein; increasing the pressure within the rotor cup to at least 2 atm; rotating the rotor cup and the fluid disposed therein at a rotor velocity set point such that a rotational shear force is imparted to the bob by the fluid; sensing a rotation of a magnetic coupling connected to the bob using an inertial measurement unit; and determining the viscosity of the fluid based on the angular acceleration of the magnetic coupling.

Although viscosity measurement of Newtonian fluid is discuss by example herein, the present disclosure is not intended to be limited to use with a particular type of fluid. For example, in certain embodiments, the present disclosure may be used to obtain viscosity profiles and/or calculate rheological properties of a non-Newtonian fluid, as would be appreciated by one of ordinary skill in the art with the benefit of the present disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are defined herein to mean one or more than one of the element that it introduces.

What is claimed is:

1. A system for measuring the viscosity of a fluid, comprising:
 a rotor cup;
 a bob disposed within the rotor cup and having a shaft rotatably coupled to the rotor cup;
 a bearing connecting the shaft of the bob to the rotor cup;
 a magnetic coupling comprising a first magnetic element connected to the shaft of the bob and a second magnetic element disposed outside the rotor cup adjacent to the first magnetic element; and
 an inertial measurement unit disposed adjacent to the second magnetic element which is capable of sensing rotation of the magnetic coupling.

2. The system of claim 1, further comprising an inner chamber defined by an inner surface of the rotor cup, wherein the inner chamber is enclosed by the rotor cup and contains the fluid.

3. The system of claim 2, wherein the rotor cup comprises at least one seal restricting fluid flow between the inner chamber and a surrounding environment.

4. The system of claim 2, wherein the inner chamber is capable of containing a pressure of at least 250 atm.

5. The system of claim 1, further comprising a heater disposed adjacent to the rotor cup.

6. The system of claim 1, further comprising a piston disposed within the rotor cup, wherein the piston creates a seal with an inner surface of the rotor cup.

7. The system of claim 1, further comprising a motor capable of rotating the rotor cup about the bob.

8. The system of claim 1, wherein the bearing includes a jewel bearing.

9. A method for measuring the viscosity of a fluid, comprising:
    containing the fluid within a rotor cup having a bob rotatably disposed therein;
    rotating the rotor cup and the fluid disposed therein;
    sensing an angular rotation property of a magnetic coupling comprising a first magnetic element connected to the bob and a second magnetic element disposed outside the rotor cup adjacent to the first magnetic element; and
    determining the viscosity of the fluid based on the angular rotation property of the magnetic coupling.

10. The method of claim 9, wherein rotating the rotor cup further comprises increasing a rotational velocity of the rotor cup to a rotor velocity set point during a ramp up period, and maintaining the rotational velocity of the rotor cup at the rotor velocity set point for a measurement period.

11. The method of claim 10, further comprising keeping the bob stationary during the ramp up period.

12. The method of claim 11, further comprising allowing the bob to rotate during the measurement period.

13. The method of claim 10, further comprising allowing the bob to rotate during the ramp up period and the measurement period.

14. The method of claim 9, further comprising heating the rotor cup.

15. The method of claim 9, further comprising separating a chamber within the rotor cup from an environment outside the rotor cup.

16. The method of claim 9, further comprising increasing the pressure within the rotor cup to at least 2 atm.

17. The method of claim 16, wherein increasing the pressure within the rotor cup includes extending a piston into the rotor cup.

18. The method of claim 9, wherein the fluid is a Newtonian fluid.

19. A method for measuring the viscosity of a fluid, comprising:
    containing the fluid within a rotor cup having a bob rotatably disposed therein;
    increasing the pressure within the rotor cup to at least 2 atm;
    rotating the rotor cup and the fluid disposed therein at a rotor velocity set point such that a rotational shear force is imparted to the bob by the fluid;
    sensing a rotation of a magnetic coupling connected to the bob using an inertial measurement unit, wherein the magnetic coupling comprises a first magnetic element connected to the bob and a second magnetic element disposed outside the rotor cup adjacent to the first magnetic element; and
    determining the viscosity of the fluid based on an angular acceleration of the magnetic coupling.

20. The method of claim 19, further comprising pressurizing a chamber within the rotor cup.

* * * * *